United States Patent
Li et al.

(10) Patent No.: US 10,568,690 B2
(45) Date of Patent: Feb. 25, 2020

(54) HIGH POWER VCSEL LASER TREATMENT DEVICE WITH SKIN COOLING FUNCTION AND PACKAGING STRUCTURE THEREOF

(71) Applicant: SANHE LASERCONN TECH CO., LTD., Sanhe (CN)

(72) Inventors: Yang Li, Beijing (CN); Delong Li, Beijing (CN)

(73) Assignee: SANHE LASERCONN TECH CO., LTD., Sanhe, Hebei (CN)

( * ) Notice: Subject to any disclaimer, the term of this patent is extended or adjusted under 35 U.S.C. 154(b) by 50 days.

(21) Appl. No.: 15/525,594

(22) PCT Filed: Dec. 7, 2014

(86) PCT No.: PCT/CN2014/093209
§ 371 (c)(1),
(2) Date: May 10, 2017

(87) PCT Pub. No.: WO2016/074300
PCT Pub. Date: May 19, 2016

(65) Prior Publication Data
US 2017/0340386 A1 Nov. 30, 2017

(30) Foreign Application Priority Data

Nov. 10, 2014 (CN) ........................ 2014 1 0643581
Nov. 10, 2014 (CN) ........................ 2014 1 0643997
(Continued)

(51) Int. Cl.
*A61B 18/00* (2006.01)
*A61B 18/20* (2006.01)
(Continued)

(52) U.S. Cl.
CPC .......... *A61B 18/203* (2013.01); *A61N 5/0616* (2013.01); *A61B 2018/0047* (2013.01);
(Continued)

(58) Field of Classification Search
CPC ........ A61B 18/203; A61B 2018/00005; A61B 2018/0047; A61N 5/00; A61N 5/0616;
(Continued)

(56) References Cited

U.S. PATENT DOCUMENTS 5,538,919 A * 7/1996 Lebby ................. H01L 23/3732
148/DIG. 95
5,698,866 A * 12/1997 Doiron ................... A61N 5/062
257/717
(Continued)

FOREIGN PATENT DOCUMENTS

CN 2514529 10/2002
CN 2614705 5/2004
(Continued)

*Primary Examiner* — Carl H Layno
*Assistant Examiner* — Michael J Lau
(74) *Attorney, Agent, or Firm* — Mark M. Friedman

(57) ABSTRACT

Disclosed is a high power VCSEL laser treatment device with a skin cooling function, comprising VCSEL array packaged on a laser heat sink, an optical transmission device arranged in front of light-exiting faces of the VCSEL array and a high-heat conductivity optical window sheet adhered to the light-exiting port end of the optical transmission device. An integrally molded cooling conduction metal piece is arranged on the outer sides of the laser heat sink, the optical transmission device, and the high-heat-conductivity optical window sheet. In addition, one or more semiconductor chilling plates are arranged between the cooling conduction metal piece and the laser heat sink. In the above-mentioned high power VCSEL semiconductor laser treatment device, the semiconductor chilling plates and the
(Continued)

VCSEL array share the heat sink, so that the inner structure is simplified.

13 Claims, 3 Drawing Sheets

(30) Foreign Application Priority Data

Nov. 10, 2014 (CN) .................... 2014 2 0680028 U
Nov. 10, 2014 (CN) .................... 2014 2 0681459 U

(51) Int. Cl.
*A61N 5/06* (2006.01)
*A61N 5/00* (2006.01)

(52) U.S. Cl.
CPC .............. *A61B 2018/00476* (2013.01); *A61N 2005/007* (2013.01)

(58) Field of Classification Search
CPC ...... A61N 2005/007; A61N 2005/0652; A61N 2005/0665; H01S 5/005; H01S 5/423; H01S 5/02252; H01S 5/02469; H01S 5/4012
USPC ........................................................... 606/9
See application file for complete search history.

(56) References Cited

U.S. PATENT DOCUMENTS

| | | | |
|---|---|---|---|
| 6,273,885 B1 | 8/2001 | Koop et al. | |
| 7,965,754 B1* | 6/2011 | Saint Clair | H01S 5/423 372/50.12 |
| 8,243,016 B2 | 8/2012 | Chen | |
| 2002/0075935 A1* | 6/2002 | Clayton | H01S 5/026 372/75 |
| 2003/0081645 A1* | 5/2003 | Uebbing | H01S 5/02292 372/101 |
| 2004/0167592 A1* | 8/2004 | Grove | A61B 18/082 607/96 |
| 2006/0274807 A1 | 12/2006 | Cho et al. | |
| 2007/0255355 A1* | 11/2007 | Altshuler | A61B 18/203 607/86 |
| 2009/0092162 A1* | 4/2009 | Huff | H01S 5/024 372/36 |
| 2009/0287195 A1* | 11/2009 | Altshuler | A46B 15/0036 606/9 |
| 2010/0007034 A1* | 1/2010 | Meadowcroft | H01L 24/48 257/784 |
| 2010/0303113 A1* | 12/2010 | Joseph | H01S 5/423 372/36 |
| 2011/0075687 A1* | 3/2011 | Gokay | H01S 3/0617 372/10 |
| 2011/0167656 A1* | 7/2011 | Huang | H01S 5/005 33/286 |
| 2011/0305254 A1* | 12/2011 | Ueki | G02B 6/4214 372/45.01 |
| 2012/0253331 A1* | 10/2012 | Liu | A61B 18/20 606/3 |
| 2013/0147050 A1* | 6/2013 | Bonner, III | H01L 29/7786 257/773 |
| 2013/0223846 A1 | 8/2013 | Joseph | |
| 2013/0253487 A1* | 9/2013 | Liu | A61B 18/203 606/9 |
| 2014/0219607 A1* | 8/2014 | Nishie | G02B 6/4204 385/33 |
| 2016/0164261 A1 | 6/2016 | Warren | |

FOREIGN PATENT DOCUMENTS

| | | |
|---|---|---|
| CN | 201082311 | 7/2008 |
| CN | 101630668 | 1/2010 |
| CN | 101667069 | 3/2010 |
| CN | 101667571 | 3/2010 |
| CN | 201430345 | 3/2010 |
| CN | 101728366 | 6/2010 |
| CN | 202960764 | 6/2013 |
| CN | 203555822 | 4/2014 |
| CN | 204275310 | 4/2015 |
| CN | 204290034 | 4/2015 |
| JP | 2003290267 | 10/2003 |

\* cited by examiner

ND PACKAGING STRUCTURE THEREOF

BACKGROUND

Technical Field

The present invention relates to a high-power semiconductor laser treatment device that uses a vertical-cavity surface-emitting laser (VCSEL) as a light source and has a skin cooling function, and also relates to an optical filling and sealing process-based VCSEL array package structure used in the high-power semiconductor laser treatment device, and belongs to the field of laser medical technologies.

Related Art

In past twenty years, high-power semiconductor lasers have been widely applied to fields such as dermatologic surgery and laser cosmetology, for example, unhairing, skin rejuvenation, wrinkle removal, pigment therapies, or physical therapies. In most treatment occasions, on the one hand, a sufficient quantity of laser energy needs to be injected into skins, and on the other hand, burning of skins by high-power laser also needs to be avoided. Therefore, most laser treatment devices need to be used together with skin cooling devices.

In a conventional high-power semiconductor laser, a contact-type skin cooling device formed by a semiconductor chilling plate and a high thermal conductive optical window sheet is a common design structure, such as semiconductor laser structures disclosed in Chinese patents ZL201220625361.1 and ZL201320713701.0. In common high thermal conductive optical window sheets, sapphire contact windows are applied most widely. The use of a sapphire as a contact window of a skin treatment device may date back to 1990S, and the disclosure in U.S. Pat. No. 6,273,885 B1 may be referred to for the detailed structure.

A conventional high-power semiconductor laser uses an edge-emitting semiconductor laser array as a laser light source. The edge-emitting semiconductor laser array is of a laminated structure and has an independent and complex laser heat sink structure, and therefore cannot share a heat sink with a semiconductor chilling plate. In this way, independent cooling heat sinks and water through structures need to be respectively designed for the skin cooling structure and the laser structure, and therefore the structure the treatment device becomes complex. For example, a double-side refrigerating semiconductor laser system for medical beautification disclosed in Chinese patent ZL201220625361.1 includes two water through blocks. A first water through block is configured to perform conduction cooling on a contact window, and a second water through block is configured to perform conduction cooling on a semiconductor laser array. The double-water-through-block structure leads to a complex inner structure of the semiconductor laser and a relatively large volume of a laser treatment head, which usually affect a visual field of an operator during skin treatment, and increase the surgical difficulty. Therefore, the operating difficulty during the laser surgery will be greatly reduced if a laser treatment handle that has a small and exquisite volume and is conveniently operated is designed.

In recent years, as manufacturing technologies of VCSELs are gradually maturing, the VCSELs have gradually implemented high-power outputs close to high-power outputs of edge-emitting semiconductor lasers. Also, the VCSELs have multiple advantages in application, such as high reliability, high temperature resistance, uniform optical distribution, high surface reflectivity, or small wavelength temperature excursion due to unique structures thereof. In the laser medical field, the VCSELs will inevitably, gradually replace the conventional edge-emitting semiconductor lasers and become main laser treatment devices in the future.

In the prior art, a package structure of a VCSEL array is shown in FIG. 1. Usually, a single VCSEL chip is directly welded on a heat dissipation substrate having a high thermal conductivity, and then a lower surface of the heat dissipation substrate is welded on a heat sink. The heat dissipation substrate has good thermal conductivity, and dissipates heat of the VCSEL array in time by means of the heat sink, to implement heat dissipation and cooling of the VCSEL array.

SUMMARY

A first technical problem to be resolved by the present invention lies in providing a high-power VCSEL laser treatment device having a skin cooling function.

Another technical problem to be resolved by the present invention lies in providing an optical filling and sealing process-based VCSEL array package structure used in the foregoing high-power VCSEL laser treatment device.

A still another technical problem to be resolved by the present invention lies in providing a high-power VCSEL using the foregoing package structure.

To achieve the foregoing objectives of the invention, the present invention uses the following technical solutions:

In one aspect of the present invention, a high-power VCSEL, laser treatment device having a skin cooling function is provided, including a laser heat sink, a VCSEL array packaged on the laser heat sink, an optical transmission device disposed in front of a light emitting surface of the VCSEL array, and a high thermal conductive optical window sheet disposed on a light emitting opening end of the optical transmission device, where an integral cooling conduction metal piece is disposed on outer sides of the laser heat sink, the optical transmission device, and the high thermal conductive optical window sheet; and one or more semiconductor chilling plates are disposed between the cooling conduction metal piece and the laser heat sink, a hot end of the semiconductor chilling plate contacting the laser heat sink, and a cold end of the semiconductor chilling plate contacting the cooling conduction metal piece.

Preferably, the cooling conduction metal piece is wrapped outside the high thermal conductive optical window sheet, the optical transmission device, and the laser heat sink; and the high thermal conductive optical window sheet is embedded in an opening at a front end of the cooling conduction metal piece; the optical transmission device is disposed in a cavity at a front part of the cooling conduction metal piece; the laser heat sink is disposed in a cavity at a rear part of the cooling conduction metal piece; and the one or more semiconductor chilling plates are disposed in a slot between the laser heat sink and the cooling; conduction metal piece.

Preferably, the optical transmission device is disposed in the cavity at the front part of the cooling conduction metal piece by means of a support piece; and a contact slot between the optical transmission device and the support piece and a contact slot between the support piece and the laser heat sink are separately sealed and fastened by means of a sealant.

Preferably, the optical transmission device is disposed in front of the laser heat sink and the VCSEL array by means of a fastening piece; and an optical pouring sealant may be filled in a slot formed by the optical transmission device, the fastening piece, and the laser heat sink.

Alternatively, the optical pouring sealant is filled and sealed in a cavity formed by the optical transmission device, the support piece, and the laser heat sink.

In another aspect of the present invention, an optical filling and sealing process-based VCSEL array package structure used in the foregoing embodiment is provided, including a VCSEL array and a laser heat sink, where the VCSEL array is packaged on the laser heat sink, and a layer of optical pouring sealant covers a surface of the VCSEL array, and the optical pouring sealant completely covers the VCSEL array.

Also, the present invention further provides a high-power VCSEL including the foregoing VCSEL array package structure.

The high-power VCSEL semiconductor laser treatment device provided in the present invention uses a VCSEL chip as a laser light source, and has a laser heat sink with a simple structure. The semiconductor chilling plate, the cooling conduction metal piece, and the high thermal conductive optical window sheet are used as a skin cooling device, and heat dissipation is performed on a hot end of the semiconductor chilling plate by means of the VCSEL heat sink, so that a heat sink is shared between the semiconductor chilling plate and the VCSEL array. The high-power VCSEL semiconductor laser treatment device has multiple advantages such as a simple structure, strong functions, easy fabrication, high reliability, or strong environmental suitability, and has broad application prospects in the laser medical field, such as dermatologic surgery and laser cosmetology. Meanwhile, a contact slot between the optical transmission device and the support piece and a contact slot between the support piece and the laser heat sink are separately sealed and fastened by means of a sealant (such as a silicone rubber), thereby achieving the waterproof, moistureproof, and dustproof effects.

In addition, the moistureproof, waterproof, and dustproof effects of the VCSEL are implemented by using an optical pouring sealant to fill a slot between the VCSEL chip and the optical window, and interface incidence loss between the VCSEL chip and the optical window is greatly reduced by means of a refractive index match between the optical pouring sealant and the optical output window, and transmittance of the laser is further improved. In addition, the high thermal conductive optical pouring sealant also has thermal conduction and cooling functions on the optical window, thereby preventing heat generation of the optical window when power is high.

DETAILED DESCRIPTION

The technical content of the present invention is described in detail below with reference to the accompanying drawings and specific embodiments.

Figure 1:
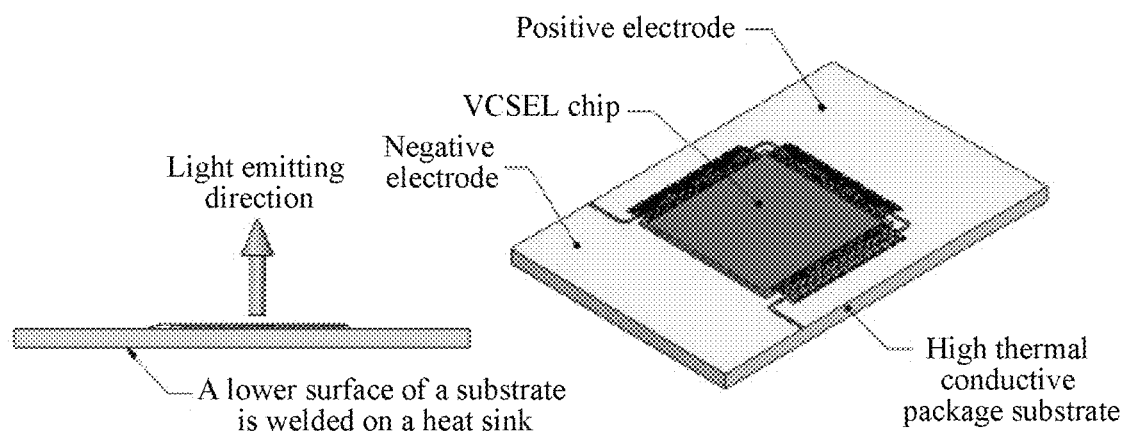
FIG. 1 is a schematic structural diagram of a package structure of a single VCSEL chip in the prior art.

A VCSEL is a semiconductor laser with a light emitting direction being perpendicular to an epitaxial wafer. A high-power VCSEL is a two-dimensional array formed by hundreds of VCSEL luminous points distributed along a surface of the epitaxial wafer, and therefore has a high optical output power. As shown in FIG. 1, a VCSEL is packaged in the following way: a whole VCSEL chip is welded on a package substrate having a high thermal conductivity, and then the substrate is welded on a laser heat sink to complete heat dissipation and cooling of the VCSEL. Due to the use of a heat sink with a simple structure in a package structure of the VCSEL, sharing of a heat sink between the laser and a semiconductor chilling plate becomes possible.

Figure 2:
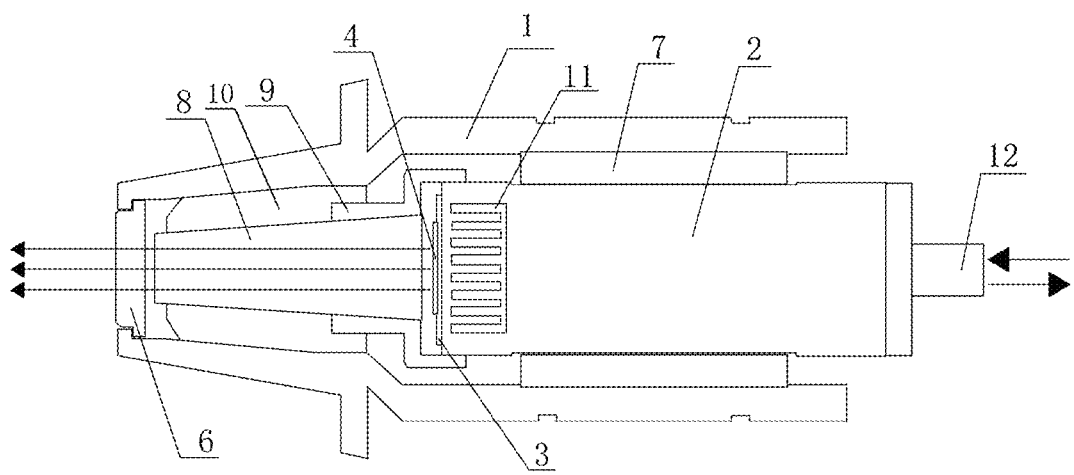
FIG. 2 is a schematic structural diagram of a high-power VCSEL laser treatment device having a skin cooling function according to a first embodiment of the present invention.

A structure of a high-power VCSEL laser treatment device provided in a first embodiment of the present invention is shown in FIG. 2. The high-power VCSEL laser treatment device includes a laser heat sink 2, a VCSEL array 4 formed by multiple VCSEL chips, an optical transmission device 8, a high thermal conductive optical window sheet 6, a cooling conduction metal piece 1, and multiple semiconductor chilling plates 7. The VCSEL array 4 is packaged on the laser heat sink 2 by a package substrate 3. The optical transmission device 8 is disposed in front of a light emitting surface of the VCSEL array 4 (that is, on the laser heat sink 2) by means of a fastening piece 9 (when the optical transmission device 8 is a light guide cone, the fastening piece 9 is a light cone sleeve), and the high thermal conductive optical window sheet 6 is disposed on a light emitting opening end of the optical transmission device 8. The integral cooling conduction metal piece 1 is disposed on outer sides of the laser heat sink 2, the optical transmission device 8, and the high thermal conductive optical window sheet 6. The cooling conduction metal piece 1 directly or indirectly contacts the optical transmission device 8 and the high thermal conductive optical window sheet 6, to perform heat dissipation on the optical transmission device 8 and the high thermal conductive optical window sheet 6. The high thermal conductive optical window sheet 6 may be directly embedded in an opening at a front end of the cooling conduction metal piece 1. The optical transmission device 8 may be disposed in a cavity at a front part of the cooling conduction metal piece 1 by means of a support piece 10. A specific configuration structure thereof is described in detail below. In addition, one or more semiconductor chilling plates 7 are disposed between the cooling conduction metal piece 1 and the laser heat sink 2. A hot end of the semiconductor chilling plate 7 contacts the laser heat sink 2 and a cold end of the semiconductor chilling plate 7 contacts the cooling conduction metal piece 1.

In the high-power VCSEL laser treatment device, skins are cooled by a skin cooling device formed by the high thermal conductive optical window sheet 6, the cooling conduction metal piece 1, and the semiconductor chilling plate 7. Heat dissipation is performed on the hot end of the semiconductor chilling plate 7 by means of the laser heat sink 2. That is, in the high-power VCSEL laser treatment device, the laser heat sink 2 is shared between the VCSEL array 4 and the skin cooling device.

Specifically, in the first embodiment shown in FIG. 2, inside the high-power VCSEL laser treatment device, the cooling conduction metal piece 1 is wrapped outside the high thermal conductive optical window sheet 6, the optical transmission device 8, and the laser heat sink 2. The high thermal conductive optical window sheet 6 is embedded in the opening at the front end of the cooling conduction metal piece 1, to form an outlet of laser energy. The optical transmission device 8 is disposed in the cavity at the front part of the cooling conduction metal piece 1 by means of the support piece 10 shown in FIG. 2. The support piece 10 may be made of a material the same as that of the cooling conduction metal piece 1, so that heat generated by the optical transmission device 8 during a laser transmission process is dissipated in time by means of the support piece 10 and the cooling conduction metal piece 1. Certainly, the support piece 10 located between the optical transmission device 8 and the cooling conduction metal piece 1 in FIG. 2 may also be integrally formed with the cooling conduction metal piece 1, so as to simplify assembly of the entire laser treatment device. The laser heat sink 2 is disposed in a cavity at a rear part (a side far from skins) of the cooling conduction metal piece 1. One or more semiconductor chilling plates 7 are disposed in a slot between the laser heat sink 2 and the cooling conduction metal piece 1 for performing refrigeration on the cooling conduction metal piece 1. The hot end of the semiconductor chilling plate 7 contacts the laser heat sink 2, and the cold end of the semiconductor chilling plate 7 contacts the cooling conduction metal piece 1, so as to transmit, by means of the laser heat sink 2, heat transmitted from the cooling conduction metal piece 1. The laser heat sink 2 is also used for performing heat dissipation on the VCSEL array 4 and the skin cooling device formed by the high thermal conductive optical window sheet 6, the cooling conduction metal piece 1, and the semiconductor chilling plate 7A micro channel structure 11 is disposed inside the laser heat sink 2. A water port 12 is disposed at a rear part of the laser heat sink 2. The water port 12 is communicated with the micro channel structure 11 inside the laser heat sink 2 for providing cooling water to perform cooling, so as to improve heat exchange efficiency of the laser heat sink 2.

In view of the above, in the high-power VCSEL laser treatment device, the VCSEL array 4 and the skin cooling device share the laser heat sink 2. Heat dissipation is performed on both the VCSEL array 4 and the semiconductor chilling plate 7 by means of the laser heat sink 2, so as to simplify an inner structure of the laser treatment device while ensuring sufficient heat dissipation and skin cooling.

An implementation structure of the skin cooling function of the high-power VCSEL laser treatment device provided in the present invention is described in detail above. Other detailed structures in the high-power VCSEL laser treatment device are introduced below.

In the first embodiment shown in FIG. 2, a package surface of the laser heat sink 2 is a plane, and multiple VCSEL chips are densely arranged on the package surface of the laser heat sink 2 to form the VCSEL array 4. The optical transmission device 8 is disposed in front of the light emitting surface of the VCSEL array 4. Specifically, the optical transmission device 8 is disposed in front of the laser heat sink 2 and the VCSEL array 4 by means of the fastening piece 9 (when a light guide cone is used, the fastening piece 9 is a light cone sleeve), and an optical pouring sealant (not shown) may be filled in a slot formed by the optical transmission device 8, the fastening piece 9, and the laser heat sink 2. In addition, to achieve waterproof, moisture-proof, and dustproof effects, a contact slot between the optical transmission device 8 and the support piece 10 and a contact slot between the support piece 10 and the laser heat sink 2 may also be separately sealed and fastened by means of a sealant (such as a silicone rubber). The sealing manner of using the optical pouring sealant and the sealing manner of using the sealant may be alternatively used.

In this embodiment, the optical transmission device 8 is an inner wall reflective optical transmission device for performing transmission and convergence on light rays emitted by the VCSEL array 4. Because the VCSEL is a circular light source and has a relatively small divergence angle (a full angle of the divergence angle is approximately 15 to 20 degrees), far field intensity whereof is in approximately flat top distribution and energy whereof is uniform, light rays emitted by the VCSEL are more easily converged and energy distribution in a far field is uniform compared with an edge-emitting semiconductor laser. In addition, the inner wall reflective optical transmission device may also reflect, to the light emitting surface of the VCSEL array 4, light rays that are reflected by a skin treatment point, Depending on extremely high reflectivity (more than 99.5%) of a surface of the VCSEL chip, the light emitting surface of the VCSEL array 4 may perform highly efficient secondary reflection on the reflected light rays that are reflected by the skin treatment point and the inner wall reflective optical transmission device, so as to sufficiently improve a utilization rate of laser and absorptivity of skins, thereby improving treatment effects.

In actual use, a reflector barrel having a polished inner wall or a light guide cone based on inner wall total reflection (which may be a parallel light cone, a step-shaped light cone, or the like) is usually used as the optical transmission device 8. The reflector barrel implements transmission and convergence of laser from a chip light emitting area to the skin treatment point in a manner of inner wall specular reflection. The light guide cone implements transmission and convergence of laser from the chip light emitting area to the skin treatment point in a manner of inner wall total reflection. To improve the light transmission efficiency of the light guide cone, optical antireflection films may be respectively evaporated on a light incident surface and a light emitting surface of the light guide cone.

In this embodiment, the high thermal conductive optical window sheet 6 abuts the light emitting opening end of the optical transmission device 8. The high thermal conductive optical window sheet 6 may be made of a material having high thermal conductivity and high light transmittance such as a sapphire or an optical-grade artificial diamond. To enhance light transmittance of the high thermal conductive optical window sheet 6, optical antireflection films may further be evaporated on both sides of the high thermal conductive optical window sheet 6.

Based on the above, in the first embodiment, the VCSEL array 4 is packaged by means of the laser heat sink 2 of which a package surface is a plane. Laser light rays are transmitted and converged by means of the inner wall reflective optical transmission device (such as a light guide cone), and skins are cooled by means of the skin cooling device formed by the high thermal conductive optical window sheet 6, the cooling conduction metal piece 1, and the semiconductor chilling plate 7. A simple structural design enables the VCSEL array 4 and the skin cooling device to share the laser heat sink 2, so as to simplify the inner structure of the high-power VCSEL laser treatment device.

In a second embodiment of the present invention, an overall structural configuration of the high-power VCSEL laser treatment device is the same as that of the first embodiment, and only a package surface of a laser heat sink 2, a package structure of a VCSEL array 4, and a light incident surface of an optical transmission device 8 differ from those of the first embodiment. The package surface of the laser heat sink 2 not only may be configured as the plane shown in FIG. 2, but also may be configured as a polygonal package surface shown in FIG. 3. In addition, when the package surface of the laser heat sink 2 is the polygon shown in FIG. 3, a light convergence effect of the VCSEL array is better.

Figure 3:
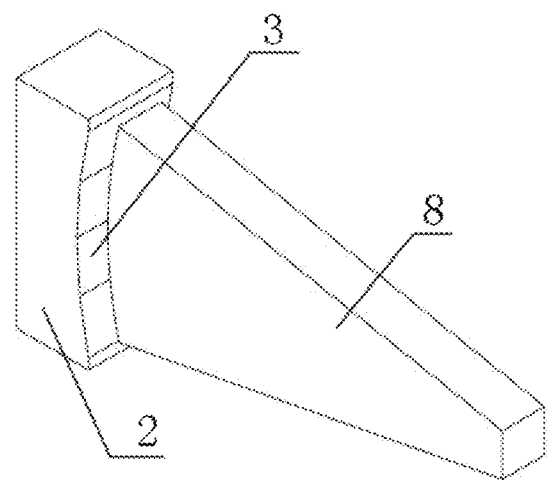
FIG. 3 is a schematic structural diagram of a VCSEL heat sink and an inner wall reflective optical transmission device according to a second embodiment of the present invention.
Figure 4:
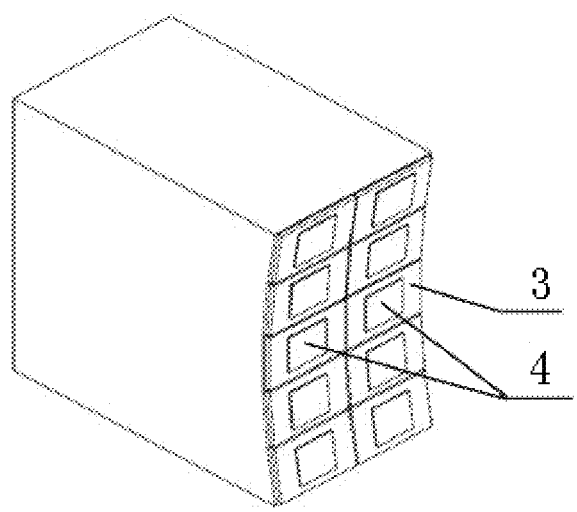
FIG. 4 is a schematic diagram of a structure in which a VCSEL array is packaged on a surface of the laser heat sink according to the second embodiment of the present invention.

As shown in FIG. 3 and FIG. 4, a cross section of the package surface of the laser heat sink 2 is a partial circumscribed polygon of a circle, and is circumscribed on a circular arc surface that uses a skin treatment point as a circle center and uses a focal length as a radius. The package surface of the laser heat sink 2 is formed by multiple small package planes at a particular angle with each other. The package surface is recessed inwards, and is approximately an arc recessed inwards. Specifically, the cross section of the package surface of the laser heat sink 2 is a partial circumscribed polygon of a circle that uses a convergent point (a focus of the VCSEL array) where the skin treatment point is located as a circle center O and uses a focal length as a radius R. Central normals of the small package planes intersect at the focus. In actual use, the convergent point may deviate to some extent, as long as the central normals of the small package planes intersect near the focus. The laser heat sink 2 converges light beams of multiple VCSEL chips to places near the position of the circle center of the arc surface, to implement optical convergence of the multiple VCSEL chips in one direction.

In the high-power VCSEL laser treatment device, all VCSEL chips in the VCSEL array 4 are packaged by means of the foregoing laser heat sink 2. As shown in FIG. 4, all VCSEL chips in the VCSEL array 4 are respectively installed on the small package planes of the arc-shaped heat sink 2, and one or more VCSEL chips may be packaged on each of the small package planes, so that orthographic projections of all VCSEL chips are distributed on an outer circumference that uses a focus as a circle center O and uses a focal length as a radius R, and central normals of all VCSEL chips interact at a position of the circle center. Therefore, all light beams of a VCSEL light emitting unit may intersect at the position of the circle center along a central normal direction of each VCSEL chip, to implement power superposition.

Correspondingly, in this embodiment, a cross section of a light incident surface of the optical transmission device 8 may be in a shape of a circular arc or a circular arc surface circumscribed polygon. Meanwhile, preferably, an inner wall of the optical transmission device 8 is parallel to a radius direction of a circle that uses a focus as a circle center and uses a focal length as a radius. A length of the optical transmission device 8 is less than a focal length of the VCSEL array 4. Highly efficient transmission of laser may be implemented by means of the optical transmission device 8, which also has a light beam compression function on laser, to implement a light beam convergence function.

When the cross section of the light incident surface of the optical transmission device 8 is in a shape of a circular arc, a circle center of the light incident surface is the same as the convergent point of the VCSEL array 4, so that the light incident surface is tangent to a light emitting surface of each VCSEL chip in the VCSEL array 4. A central normal of the light emitting surface of the VCSEL chip is perpendicular to the light incident surface of the optical transmission device 8. Laser rays emitted by the VCSEL chip may be perpendicularly incident into the optical transmission device 8, and each divergence angle of the VCSEL may be compressed.

When the cross section of the light incident surface of the optical transmission device 8 is in a shape of a circular arc surface circumscribed polygon, the light incident surface may be formed by multiple small planes at a particular angle with each other, and a circle center thereof is homocentric with a circle center of the laser heat sink 4. A central normal of a VCSEL chip packaged on each small package plane may be enabled to be perpendicular to a small plane corresponding thereto by enabling each small plane of the optical transmission device 8 to correspond and be parallel to a single small package plane of the laser heat sink 2, so that laser emitted by the VCSEL chip may be directly incident into the optical transmission device 8, and each divergence angle of the VCSEL may be compressed. In addition, the configuration of the circular arc surface circumscribed polygon greatly reduces a distance between the VCSEL array 4 and the optical transmission device 8, and reduces laser escape at the slot.

In the second embodiment of the present invention, in the high-power VCSEL semiconductor laser treatment device, not only the skin cooling device is improved to simplify an inner structure thereof, but also package of the VCSEL array is improved to effectively improve optical convergence and utilization rate of the VCSEL.

Based on the above, the high-power VCSEL semiconductor laser treatment device uses a VCSEL chip as a laser light source, and has the laser heat sink with a simple structure. Meanwhile, the high-power VCSEL semiconductor laser treatment device uses a semiconductor chilling plate, a cooling conduction metal piece, and a high thermal conductive optical window sheet as a skin cooling device. A hot end of the semiconductor chilling plate and the VCSEL array share the laser heat sink, so that a cooling structure and a water through structure of the entire device become extremely simple when skin cooling is performed. The device has multiple advantages such as a simple structure, strong functions, easy fabrication, low costs, high reliability, or strong environmental and has broad application prospects in the laser medical field, such as dermatologic surgery and laser cosmetology.

The high-power VCSEL laser treatment device having a skin cooling function provided in the present invention is introduced above. A package structure that seals a surface of a VCSEL chip by means of an optical pouring sealant in the present invention and application thereof in the field of high-power semiconductor lasers are described below with reference to FIG. 5 and FIG. 6.

In actual use of a VCSEL, to prevent the surface of the VCSEL chip from being affected by condensation, humidity, dust, or the like, sealing processing usually needs to be performed on a VCSEL, and output and application are performed by means of an optical window. Generally, a conventional method is to use an O-shaped ring or a sealant to seal slots among an optical window, a covering housing, a VCSEL chip, and a laser heat sink, so as to isolate a slot in front of the VCSEL chip from outer air. The sealing method is usually complex and cumbersome, and affects an overall appearance structure. Therefore, a VCSEL array package structure with a simple structure and a good isolation effect needs to be provided.

Figure 5:
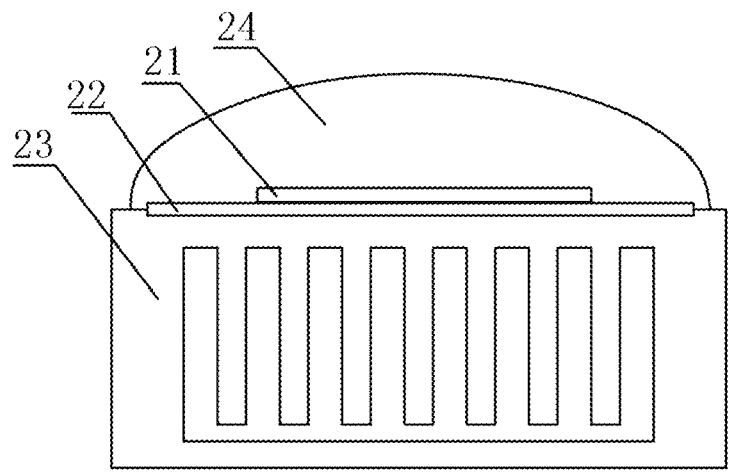
FIG. 5 is a schematic diagram of a package structure of an optically filled and sealed VCSEL.

As shown in FIG. 5, a VCSEL array package structure provided in the present invention includes a VCSEL array 21, a substrate 22, and a laser heat sink 23. The VCSEL array 21 is packaged on the laser heat sink 23 by means of the substrate 22. Specifically, the VCSEL chip may be directly welded on an upper surface of the substrate 22, and then a lower surface of the substrate 22 is welded on the laser heat sink 23. The substrate 22 has a good thermal conductivity. Heat of the VCSEL array 21 may be conducted in time by means of the substrate 22 and the laser heat sink 23, to implement heat dissipation and cooling of the VCSEL array 21.

In the package structure provided in this embodiment of the present invention, an optical pouring sealant 24 is introduced for the first time. A layer of optical pouring sealant 24 is directly covered, filled and sealed, and cured on a surface of the VCSEL array 21, to satisfy an airtightness requirement of a VCSEL. The optical pouring sealant 24 completely covers the VCSEL array 21, and spreads on a surface of the entire laser heat sink 23, so that the VCSEL chip is completely immersed in the sealant, to implement good airtightness. The VCSEL array package structure has excellent waterproof, moistureproof, and dustproof functions, and may be adapted to a severe working environment, for example, an environment with a high temperature of more than 80 degrees Celsius and a relative humidity of 100%, or may even normally work under water. The package structure can effectively protect the VCSEL chip and prevent environmental disruption, and has extremely high reliability. The package structure provided in this embodiment of the present invention has a simple structure, a small and exquisite volume, and low costs, and the used optical filling and sealing process is also extremely simple and easy to implement.

The optical pouring sealant 24 may directly and naturally cover the VCSEL array 21 to form a smooth outer surface (shown in FIG. 5), or may also be filled and sealed and cured by means of an outer mold to form an optical window having a regular arbitrary geometrical shape for performing optical shaping on laser light beams emitted by the VCSEL chip. For example, the optical pouring sealant 24 may be cured into a tapered step, so that the optical pouring sealant 24 is also used as an optical window. When the optical pouring sealant 24 is used as an optical window having a regular geometrical shape after being cured, outer optical devices of the VCSEL are saved to facilitate optical shaping of light beams emitted by the VCSEL. In addition, the optical pouring sealant 24 may also be used together with another optical window for VCSEL outputs, that is, the optical pouring sealant 24 is used to directly fill a slot between the VCSEL chip and the optical window to seal the VCSEL. The present invention provides an embodiment to describe this. Refer to the following for detailed content.

In actual use, the optical pouring sealant may be a soft glue or a hard glue according to specific application requirements. Different fluorescent powder for wavelength conversion may also be added into the optical pouring sealant to implement optical output with high brightness, different wavelengths, or even mixed wavelengths (such as white light), so as to enrich extensive application of the VCSEL in the field of commercial illumination.

In this embodiment of the present invention, the optical pouring sealant 24 for filling and sealing has high thermal conductivity, high transmittance, and high thermal endurance, and may be adapted to high-power optical output power and high temperature working attributes of the VCSEL. During a working process of a VCSEL array, heat of the optical pouring sealant 24 may be conducted and cooled by means of a VCSEL surface, the substrate 22, and the laser heat sink 23, and therefore overburning may be prevented, to satisfy the requirement for heat dissipation.

Figure 6:
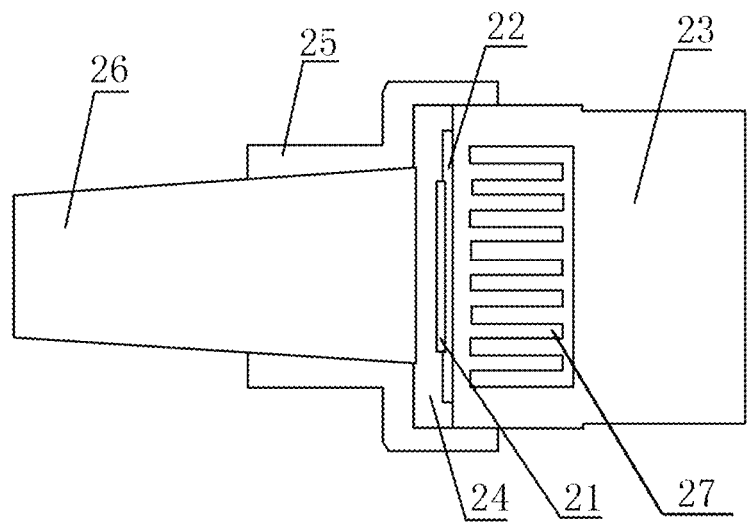
FIG. 6 is a schematic structural diagram of a high-power VCSEL that is optically filled and sealed.

An embodiment of a high-power VCSEL using the foregoing package structure is introduced below. The embodiment may be directly applied to the foregoing high-power VCSEL laser treatment device having a skin cooling function. As shown in FIG. 6, the high-power VCSEL includes: a VCSEL array 21, a substrate 22, and a laser heat sink 23. The VCSEL array 21 is installed on the laser heat sink 23 by means of the substrate 22. An optical window 26 is disposed in front of a light emitting surface of the VCSEL array 21. The optical window 26 is fastened on a laser heat sink 23 by means of a covering housing 25, so as to form a slot among the laser heat sink 23, the optical window 26, and the covering housing 25. To seal the VCSEL array 21, an optical pouring sealant 24 with high thermal conductivity, high transmittance, and high thermal endurance is filled in the slot. A VCSEL chip is completely immersed in the sealant, to implement good airtightness, and achieve waterproof, moistureproof, and dustproof functions.

The optical filling and sealing structure implements direct incidence match from a laser chip to the optical window 26 without intervention of air. In addition, if the optical pouring sealant 24 is made of a material having a refractive index close to that of the optical window 26, interface incidence loss between the VCSEL chip and the optical window 26 may be greatly reduced, and transmittance of the laser is further improved. By plating an antireflection film on an emission surface of the optical window 26, optical emitting interface loss may further be reduced. In actual use, the optical window 26 may use a planar optical window, an optical lens, or an optical prism, a light cone, or the like of a specific type, to fit optical shaping of light beams.

In addition, because the optical pouring sealant 24 is a material having high thermal conductivity, high transmittance, and high thermal endurance, the optical pouring sealant not only is a filling and sealing medium, but also is an optical conductive medium and a thermal-conducting medium. The optical pouring sealant 24 also has thermal conduction and cooling functions on the optical window 26, to prevent heat generation of the optical window 26 when power is high, to be adapted to high-power optical output power and high temperature working attributes of the VCSEL. To improve heat dissipation of the high-power VCSEL, a micro cooling channel 27 is disposed in the laser heat sink 23 for water through cooling.

In view of the above, when the present invention provides the high-power VCSEL laser treatment device having a skin cooling function, the present invention introduces the optical pouring sealant into package of the high-power VCSEL for the first time, to effectively resolve the sealing problem of the VCSEL. The VCSEL array is sealed by means of the optical pouring sealant, to implement moistureproof, waterproof, and dustproof functions of the VCSEL, so that the VCSEL may be adapted to a severe working environment, for example, an environment with a high temperature of more than 80 degrees Celsius and a relative humidity of 100%, or may even normally work under water. The package structure can effectively protect the VCSEL chip and prevent environmental disruption, and has extremely high reliability.

According to the semiconductor layer using the foregoing package structure provided in the present invention, by using an optical pouring sealant to fill a slot between the VCSEL chip and the optical window, direct incidence match from the laser chip to the optical window may be implemented without intervention of air, and moistureproof, waterproof, and dustproof functions of the VCSEL are also implemented; in addition, interface incidence loss between the VCSEL chip and the optical window may be greatly reduced by means of a refractive index match between the optical pouring sealant and the optical output window, and transmittance of the laser is further improved.

The foregoing describes the high-power VCSEL laser treatment device having a skin cooling function and the package structure thereof provided in the present invention in detail. For a person of ordinary skill in the art, any obvious modification made to the present invention without departing from the essential spirit of the present invention constitutes infringement on the patent right of the present invention, and corresponding legal liabilities shall be born.

What is claimed is:

1. A high-power VCSEL laser treatment device having a skin cooling function, comprising a laser heat sink, a VCSEL array packaged on the laser heat sink, an optical transmission device disposed in front of a light emitting surface of the VCSEL array, and a high thermal conductive optical window sheet disposed on a light emitting opening end of the optical transmission device, wherein
    a cross section of a package surface of the laser heat sink is a partial circumscribed polygon of a circle, and the partial circumscribed polygon is circumscribed on a circular arc surface that uses a skin treatment point as a circle center and uses a focal length as a radius; the package surface being formed by multiple small package planes at a particular angle with each other, the package surface being recessed inwards, and central normals of the small package planes intersecting at a focus position; and all VCSEL chips in the VCSEL array are respectively installed on the small package planes of the heat sink, and each of the small package planes is used to package one or more VCSEL chips;
    an integral cooling conduction metal piece is disposed on outer sides of the laser heat sink, the optical transmission device, and the high thermal conductive optical window sheet; and one or more semiconductor chilling plates are disposed between the cooling conduction metal piece and the laser heat sink, a hot end of the semiconductor chilling plate contacting the laser heat sink, and a cold end of the semiconductor chilling plate contacting the cooling conduction metal piece, the heat sink is used to dissipate heat transferred from the high thermal conductive optical window sheet that is in contact with skin to the cooling conduction metal piece; the heat sink is shared by the cooling conduction metal piece and the VCSEL array.

2. The high-power VCSEL laser treatment device according to claim 1, wherein:
    the cooling conduction metal piece is wrapped outside the high thermal conductive optical window sheet, the optical transmission device, and the laser heat sink; and
    the high thermal conductive optical window sheet is embedded in an opening at a front end of the cooling conduction metal piece; the optical transmission device is disposed in a cavity at a front part of the cooling conduction metal piece; the laser heat sink is disposed in a cavity at a rear part of the cooling conduction metal piece;
    and the one or more semiconductor chilling plates are disposed in a slot between the laser heat sink and the cooling conduction metal piece.

3. The high-power VCSEL laser treatment device according to claim 2, wherein:
    the optical transmission device is disposed in the cavity at the front part of the cooling conduction metal piece by means of a support piece; and a contact slot between the optical transmission device and the support piece and a contact slot between the support piece and the laser heat sink are sealed and fastened by means of a sealant.

4. The high-power VCSEL laser treatment device according to claim 3, wherein:
    the support piece is made of a material the same as that of the cooling conduction metal piece.

5. The high-power VCSEL laser treatment device according to claim 3, wherein:
    the support piece is integrally formed with the cooling conduction metal piece.

6. The high-power VCSEL laser treatment device according to claim 1, wherein:
    the optical transmission device is disposed in front of the laser heat sink and the VCSEL array by means of a fastening piece.

7. The high-power VCSEL laser treatment device according to claim 6, wherein:
    an optical pouring sealant is filled in a slot formed by the optical transmission device, the fastening piece, and the laser heat sink.

8. The high-power VCSEL laser treatment device according to claim 1, wherein:
    the optical transmission device is a reflector barrel having a polished inner wall or a light guide cone based on inner wall total reflection.

9. The high-power VCSEL laser treatment device according to claim 1, wherein:
    a cross section of a light incident surface of the optical transmission device is in a shape of a circular arc or a circular arc surface circumscribed polygon.

10. The high-power VCSEL laser treatment device according to claim 1, wherein:
    the high thermal conductive optical window sheet is a sapphire or an optical-grade artificial diamond.

11. The high-power VCSEL laser treatment device according to claim 1, wherein:
    a micro channel structure is designed inside the laser heat sink.

12. The high-power VCSEL laser treatment device according to claim 1, wherein:
    an inner wall of the optical transmission device is parallel to a radius direction of a circle that uses the focus as a circle center and uses the focal length as a radius.

13. The high-power VCSEL laser treatment device according to claim 1, wherein:
    an emission opening of the optical transmission device is at the circle center or near the circle center.

* * * * *